US008594803B2

(12) United States Patent
Magdych (10) Patent No.: US 8,594,803 B2
(45) Date of Patent: Nov. 26, 2013

(54) BIOTHERMAL POWER GENERATOR (75) Inventor: James Stephen Magdych, Keizer, OR (US)

(73) Assignee: Borealis Technical Limited (GI)

( * ) Notice: Subject to any disclaimer, the term of this patent is extended or adjusted under 35 U.S.C. 154(b) by 1348 days.

(21) Appl. No.: 11/900,780

(22) Filed: Sep. 12, 2007

(65) Prior Publication Data

US 2008/0065172 A1      Mar. 13, 2008

(30) Foreign Application Priority Data

Sep. 12, 2006  (GB) .................................. 0617934.5

(51) Int. Cl.
*A61N 1/00*       (2006.01)

(52) U.S. Cl.
USPC .......................................................... 607/61

(58) Field of Classification Search
USPC ...................................................... 607/35, 61
See application file for complete search history.

(56) References Cited

U.S. PATENT DOCUMENTS

| | | |
|---|---|---|
| 3,740,592 A | 6/1973 | Engdahl et al. |
| 4,011,582 A | 3/1977 | Cline et al. |
| 4,039,352 A | 8/1977 | Marinescu |
| 4,063,965 A * | 12/1977 | Cline et al. ............. 438/455 |
| 4,667,126 A * | 5/1987 | Fitzpatrick ............. 310/306 |
| 4,686,162 A | 8/1987 | Stangl et al. |
| 5,023,671 A | 6/1991 | DiVincenzo et al. |
| 5,068,535 A | 11/1991 | Rabalais |
| 5,119,151 A | 6/1992 | Onda |
| 5,229,320 A | 7/1993 | Ugajin |
| 5,233,205 A | 8/1993 | Usagawa et al. |
| 5,247,223 A | 9/1993 | Mori et al. |
| 5,332,952 A | 7/1994 | Ugajin et al. |
| 5,336,547 A | 8/1994 | Kawakita et al. |
| 5,371,388 A | 12/1994 | Oda |
| 5,432,362 A | 7/1995 | Lippens et al. |
| 5,503,963 A | 4/1996 | Bifano |
| 5,504,388 A | 4/1996 | Kimura et al. |
| 5,521,735 A | 5/1996 | Shimizu et al. |

(Continued)

FOREIGN PATENT DOCUMENTS

| | | |
|---|---|---|
| DE | 3404137 A1 | 8/1985 |
| DE | 3818192 A1 | 12/1989 |

(Continued)

OTHER PUBLICATIONS

Chou et al., "Imprint Lithography with 25 Namometer Resolution", Science, Apr. 5, 1996, pp. 85-87, vol. 272.

(Continued)

*Primary Examiner* — Christopher D Koharski
*Assistant Examiner* — Nadia Ahmad (57) ABSTRACT

An implantable assembly is disclosed comprising a diode device charging assembly having the means for transferring thermal energy from a living organism to a diode device, means for creating electrical energy from said thermal energy, and means for charging an implantable device with said electrical current. The diode device of this invention is a thermo-tunneling or thermionic converter. In a preferred embodiment the electrodes of the diode device have been modified to reduce their work function by through the addition a periodically repeating structure comprised of one or more indentations of the dimensions so as to create de Broglie wave interference, leading to a change in electron work function. The implantable assembly utilizes a temperature difference in a body to efficiently generate energy to be harnessed by a wide range of devices.

20 Claims, 7 Drawing Sheets

(56) References Cited

U.S. PATENT DOCUMENTS

| | | | |
|---|---|---|---|
| 5,579,232 | A | 11/1996 | Tong et al. |
| 5,604,357 | A | 2/1997 | Hori |
| 5,654,557 | A | 8/1997 | Taneya et al. |
| 5,675,972 | A | 10/1997 | Edelson |
| 5,699,668 | A | 12/1997 | Cox |
| 5,705,321 | A | 1/1998 | Brueck et al. |
| 5,719,407 | A | 2/1998 | Ugajin |
| 5,722,242 | A | 3/1998 | Edelson |
| 5,772,905 | A | 6/1998 | Chou |
| 5,889,735 | A * | 3/1999 | Kawata et al. ............ 368/64 |
| 5,917,156 | A | 6/1999 | Nobori et al. |
| 6,117,344 | A | 9/2000 | Cox et al. |
| 6,214,651 | B1 | 4/2001 | Cox |
| 6,225,205 | B1 | 5/2001 | Kinoshita |
| 6,281,514 | B1 | 8/2001 | Tavkhelidze |
| 6,309,580 | B1 | 10/2001 | Chou |
| 6,417,060 | B2 | 7/2002 | Tavkhelidze et al. |
| 6,495,843 | B1 | 12/2002 | Tavkhelidze |
| 6,531,703 | B1 | 3/2003 | Tavkhelidze |
| 6,640,137 | B2 * | 10/2003 | MacDonald ............ 607/35 |
| 6,680,214 | B1 | 1/2004 | Tavkhelidze et al. |
| 6,720,704 | B1 * | 4/2004 | Tavkhelidze et al. ....... 310/306 |
| 6,908,861 | B2 | 6/2005 | Sreenivasan et al. |
| 6,980,861 | B1 * | 12/2005 | Kleine ............ 607/30 |
| 2001/0046749 | A1 | 11/2001 | Tavkhelidze et al. |
| 2003/0068431 | A1 | 4/2003 | Taliashvili et al. |
| 2003/0221608 | A1 | 12/2003 | Mori |
| 2004/0174596 | A1 | 9/2004 | Umeki |
| 2004/0206881 | A1 | 10/2004 | Tavkhelidze et al. |
| 2005/0145836 | A1 | 7/2005 | Tavkhelidze et al. |
| 2006/0093872 | A1 * | 5/2006 | Howard et al. ............ 429/9 |
| 2007/0013055 | A1 * | 1/2007 | Walitzki ............ 257/717 |
| 2009/0326611 | A1 * | 12/2009 | Gillbe ............ 607/61 |

FOREIGN PATENT DOCUMENTS

| | | |
|---|---|---|
| EP | 0437654 A1 | 7/1991 |
| JP | 03155376 A | 7/1991 |
| JP | 4080964 A | 3/1992 |
| JP | 05226704 A | 9/1993 |
| WO | WO-99/13562 A1 | 3/1999 |
| WO | WO-99/64642 A1 | 12/1999 |
| WO | WO-00/59047 A1 | 10/2000 |
| WO | WO-02/47178 A2 | 6/2002 |
| WO | WO-03/083177 A3 | 10/2003 |
| WO | WO-2004/040617 A2 | 5/2004 |
| WO | WO-2006/055890 A2 | 5/2006 |

OTHER PUBLICATIONS

Hishinuma et al., "Refrigeration by combined tunneling and thermionic emmission in vacuum: Use of nanometer scale design", Appl Phys Lett, Apr. 23, 2001, pp. 2572-2574, vol. 78, No. 17.

Sungtaek Ju et al., "Study of interface effects in thermoelectric microfefrigerators", Journal of Applied Physics, Oct. 1, 2000, pp. 4135-4139, vol. 88, No. 7.

* cited by examiner

BIOTHERMAL POWER GENERATOR

This application claims the benefit of U.K. Patent Application No. GB0617934.5, filed Sep. 12, 2006, said document incorporated herein in its entirety by reference.

BACKGROUND OF THE INVENTION

This present invention relates to a device for providing a permanent source of energy through a temperature gradient in a living body, comprising a diode device.

The mammalian body is a natural producer of thermal energy. In recent years, researchers have looked towards the body as a potential source of usable energy. The conversion of a body's thermal energy into electric energy creates a potential for medical devices and wearable devices that are powered by body heat.

For example, U.S. Pat. No. 5,889,735 discloses a thermoelectrically powered wristwatch that utilizes a temperature difference between a human body and its surroundings to generate a voltage to power a device such as a wristwatch. Similar to the concept that a temperature difference exists between the body and its surroundings is the concept that there exists differences in temperature within one body. Further, U.S. Pat. No. 6,640,137 discloses a biothermal power source for a device implanted within the human body that is comprised of a thermoelectric module for converting thermal energy to electrical energy. This device is said to produce a power output of 100 microwatts from a temperature differential of between 1 to 5 degrees Celsius.

However, because thermoelectric devices are only 5-8% efficient, the low power output of such devices requires that thousands of thermocouples be built into one device in order to generate the energy necessary to power the device (or to continuously trickle-charge the batteries). This would be difficult to manufacture, and as of yet, only tens of thermocouples have been arrayed. Thus there is a need to provide a biothermal power source that has a higher percentage of practical efficiency Recent technology has been developed to provide such a power source. FIGS. 1-5 illustrate some embodiments of such power sources having a higher percentage of practical efficiency.

Figure 1:
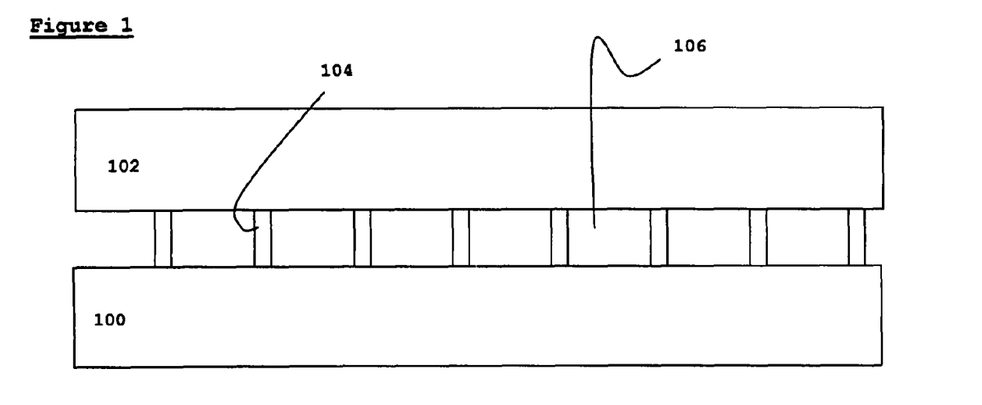
FIG. 1 is a diagrammatic representation of a thermotunneling or thermionic converter.

U.S. Patent App. Pub. No. 2007/0013055 discloses a thermotunneling/thermionic converter. A preferred embodiment of this diode device is shown in FIG. 1 in which silicon wafers 100 and 102 have their inner surfaces substantially facing one another, and a spacer or plurality of spacers 104 positioned between them. Preferably, silicon wafers 100 and 102 have matching surfaces, that where one has an indentation the other has a protrusion. Thus when matched, the two surfaces are substantially equidistant from each other. In a preferred embodiment, a vacuum 106 is introduced. In this design, active piezo control is not required to maintain the gap, making the device inexpensive. The use of active elements is not required due to the mechanical properties of silicon, such that if a small particle is trapped in between two silicon wafers, a non-bonded area of 5000 times the size (height) of the particle is created. Therefore the spacers consisting of a dot of silicon oxide topped by a protective layer will have the effect of keeping the two silicon wafers at a desired distance.

Figure 2:
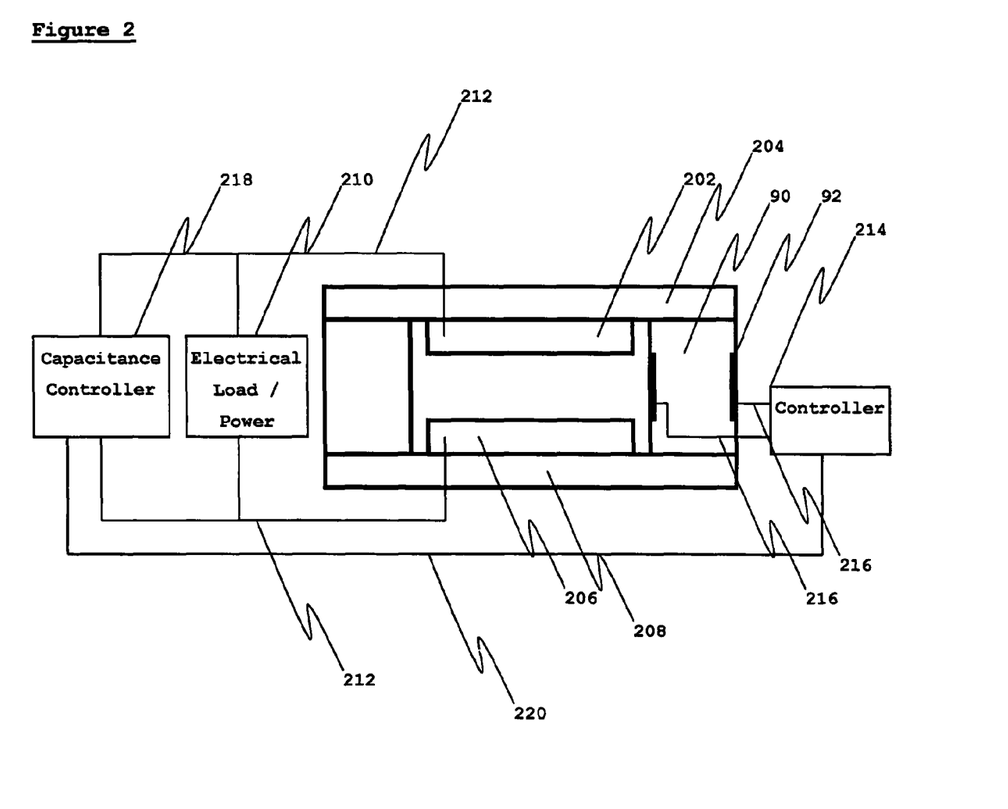
FIG. 2 is a diagrammatic representation of a thermionic vacuum diode device with adjustable electrodes.

U.S. Pat. No. 6,720,704 discloses a thermionic vacuum diode device with adjustable electrodes. A preferred embodiment of this diode device is depicted in FIG. 2, in which a first electrode 202, disposed on substrate 204, is attached to the end of actuator tube 90, and a second electrode 206, disposed on substrate 208, is attached to the other end of tube 90. The two electrodes are also connected to an electrical load or power supply 210 by means of wires 212. Actuator tube 90 has electrodes 92 disposed on its surface which are connected to controller 214 via wires 216. This controller sets the separation of electrodes 202 and 206. Electrodes 202 and 206 may also be connected to capacitance controller 218 which is able to assess the separation of the electrodes, and the separation of the electrodes may be accurately controlled via a feedback loop 220 to controller 214. Typically, the electrode separation is of the order of 0.1 to 100 nm. In a preferred embodiment, electrodes 202 and 206 may be formed as depicted in FIG. 3.

Figure 3:
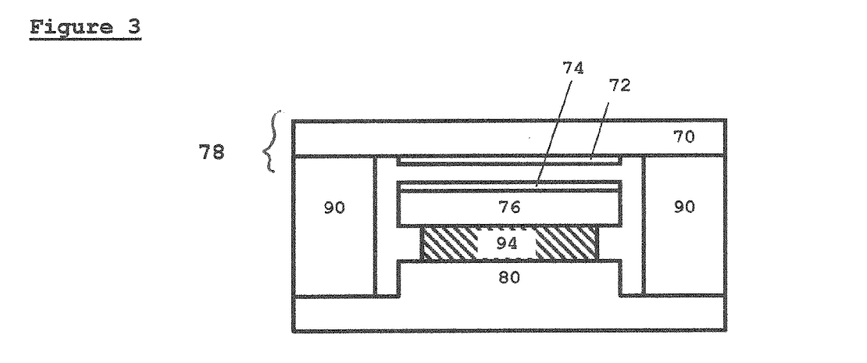
FIG. 3 is a diode device having a tubular housing/actuator.

Referring now to FIG. 3, composite 80 is any material which has a similar thermal expansion coefficient to quartz and can be bonded to quartz. Preferably, composite 80 is a molybdenum disc. Electrically conducting paste 94, preferably silver paste, lies upon the upper surface of the molybdenum disc and is in contact with a composite 78. Composite 78 is preferably a matching electrode pair precursor, such as shown in step 130 of WO99/13562 or U.S. Pat. No. 6,417,060, or is more preferably a layer of titanium 72 deposited on substrate 70, and a layer of silver 74 further deposited on the layer of titanium. A further layer of copper 76 is grown electrochemically on the layer of silver. Ideally, substrate 70 is a silicon wafer, and is polished at least around its periphery where it is in contact with tube 90. Alternatively, composite 78 is composite 79 depicted in FIG. 4. Though upon formation and at first contact with paste 94, composite 78 is a single unit, high pressure followed by heat causes the composite to open, as depicted in FIG. 3, forming a pair of matching electrodes 72 and 74.

Figure 4:
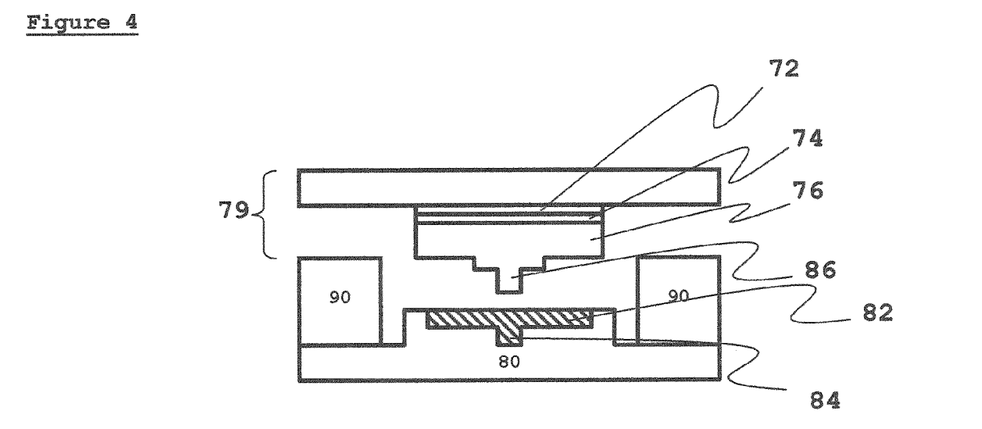
FIG. 4 shows one preferred embodiment of a diode device.

In a further embodiment, depicted in FIG. 4, substrate/composite 80 has a depression 82 across part of its surface. Substrate/composite 80 also has a locating hole 84 in its surface. An additional feature of this embodiment is alignment pin 86, which is premachined, and is attached to the composite 79 at the layer of copper 76. The diameter of the alignment pin is the same as the diameter of the locating hole which results in a tight fit between the alignment pin 86 and the locating hole 84 when the pin seats in the locating hole. The tight fit ensures that electrodes 72 and 74 do not slide relative to one another.

Figure 5:
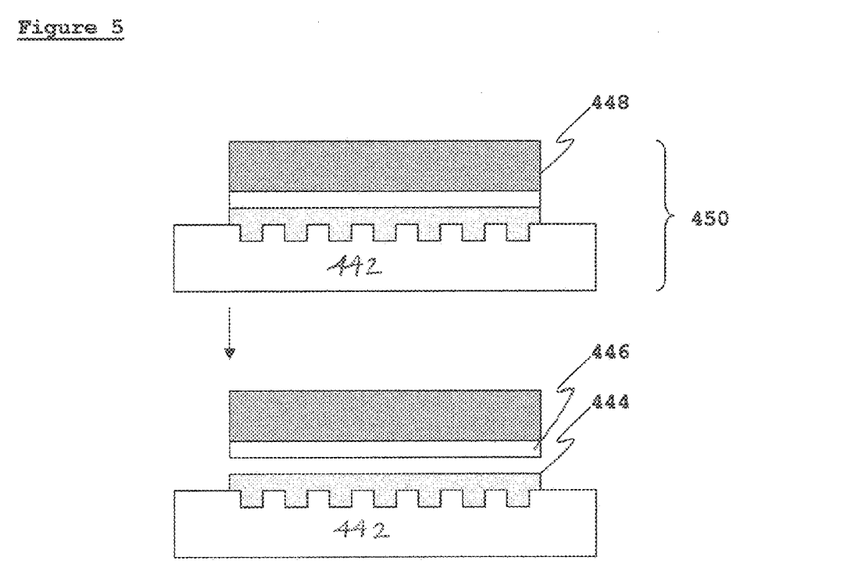
FIG. 5 shows a diode device having an indented surface.

U.S. Patent App. Pub. No. 2005/0147841, as seen in FIG. 5, discloses an electrode for a diode device having an indented surface. The indents are formed on wafer 442 by means of laser, chemical or other means for etching a geometric pattern on the surface of solid materials such as silicon, metal, and the like. Preferably, the one or more indents should have a depth approximately 5 to 20 times a roughness of the material's surface and a width approximately 5-15 times the material's depth. It is also preferable that the indents be substantially sharp and substantially perpendicular to one another. Such indents alter the distribution of quantum states within a volume limited by a potential energy barrier and promote the transfer of elementary particles across a potential energy barrier. In one embodiment, the electrode is consists of a layer of silver 444 upon indented wafer 442, followed by a layer of titanium 446, upon which a layer of copper 448 is grown electrochemically to form a composite 450. When the composite 450 is opened, as shown in FIG. 5, it forms a pair of matching electrodes that can be utilized to make diode devices.

U.S. Pat. Nos. 6,281,514, 6,495,843, and 6,531,703 disclose methods for promoting the passage of electrons at or through a potential barrier comprising providing a potential barrier having a geometrical shape for causing de Broglie interference between electrons. In another embodiment, the invention provides an electron-emitting surface having a series of indents. The depth of the indents is chosen so that the probability wave of the electron reflected from the bottom of the indent interferes destructively with the probability wave of the electron reflected from the surface. This results in the increase of tunneling through the potential barrier. In further embodiments, the invention provides vacuum diode devices, including a vacuum diode heat pump, a thermionic converter and a photoelectric converter, in which either or both of the electrodes in these devices utilize said electron-emitting surface. In yet further embodiments, the invention provides devices in which the separation of the surfaces in such devices is controlled by piezo-electric positioning elements. A further embodiment provides a method for making an electron-emitting surface having a series of indents.

U.S. Pat. No. 6,680,214 and U.S. Pat. App. Pub. No. 2004/0206881 disclose methods for the induction of a suitable band gap and electron emissive properties into a substance, in which the substrate is provided with a surface structure corresponding to the interference of electron waves. Lithographic or similar techniques are used, either directly onto a metal mounted on the substrate, or onto a mold which then is used to impress the metal. In a preferred embodiment, a trench or series of nano-sized trenches are formed in the metal.

U.S. Pat. No. 6,117,344 discloses methods for fabricating nano-structured surfaces having geometries in which the passage of electrons through a potential barrier is enhanced. The methods use combinations of electron beam lithography, lift-off, and rolling, imprinting or stamping processes.

WO9964642 discloses a method for fabricating nanostructures directly in a material film, preferably a metal film, deposited on a substrate. In a preferred embodiment a mold or stamp having a surface which is the topological opposite of the nanostructure to be created is pressed into a heated metal coated on a substrate. The film is cooled and the mold is removed. In another embodiment, the thin layer of metal remaining attached to the substrate is removed by bombarding with a charged particle beam.

WO04040617 offers a method which blocks movement of low energy electrons through a thermoelectric material. This is achieved using a filter which is more transparent to high energy electrons than to low energy ones. A tunnel barrier on the path of the electrons is used as filter. The filter works on the basis of the wave properties of the electrons. The geometry of the tunnel barrier is such that the barrier becomes transparent for electrons having certain de Broglie wavelength. If the geometry of the barrier is such that its transparency wavelength matches the wavelength of high energy electrons it will be transparent for high energy electrons and will block low energy ones by means of tunnel barrier.

Figure 6:
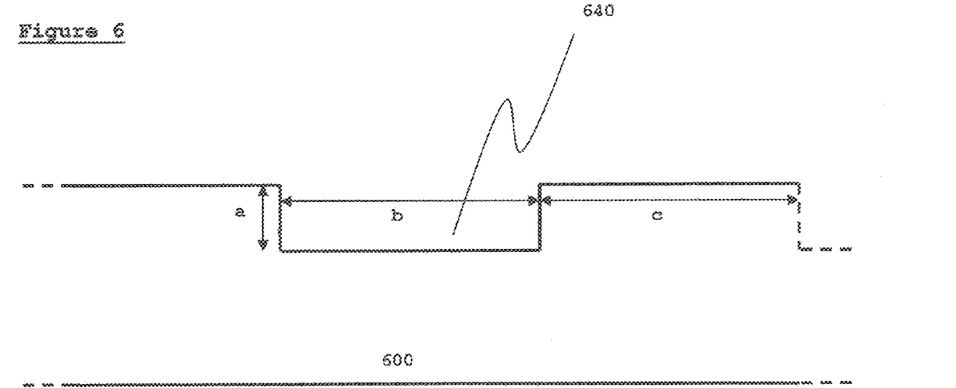
FIG. 6 is a cross sectional view of a modified electrode.

In WO03/083177, the use of electrodes having a modified shape and a method of etching a patterned indent onto the surface of a modified electrode are disclosed. The patterned indent increases the Fermi energy level inside the modified electrode, leading to a decrease in electron work function. FIG. 6 shows the shape and dimensions of a modified thin metal film 600. Indent 640 on metal substrate 600 has a width b and a depth a, and the separation between the indents is c. Preferably distances b and c are substantially equal. Preferably distance b is of the order of 2 μm or less. Experimental observations using a Kelvin probe indicate that the magnitude of a reduction in apparent work function increases as distance a is reduced. Utilization of e-beam lithography to create structures of the kind shown in FIG. 6 may allow indents to be formed in which distance b is 200 nm or less. Distance a is of the order of 20 nm or less, and is preferably of the order of 5 nm. Metal film 600 is given sharply defined geometric patterns or indents 640 of a dimension that creates a De Broglie wave interference pattern that leads to a decrease in the electron work function, thus facilitating the emissions of electrons from the surface and promoting the transfer of elementary particles across a potential barrier. The surface configuration of film 600 may resemble a corrugated pattern of squared-off, "u"-shaped ridges and/or valleys. Alternatively, the pattern may be a regular pattern of rectangular "plateaus" or "holes," where the pattern resembles a checkerboard. The walls of indent 640 should be substantially perpendicular to one another, and its edges should be substantially sharp.

BRIEF SUMMARY OF THE INVENTION

In accordance with the present invention, there is provided a biothermal power generator comprised of a diode device, which utilizes a temperature differential in the body for converting thermal energy to electric energy. The device thus comprises a heat source in contact with a first surface of the diode device; a heat sink in contact with a second surface of the diode device; and means for transferring thermal energy from the heat source through the diode device to the heat sink. The heat source is a living organism.

In one embodiment the power generating assembly comprises a diode device which is a thermionic diode device having adjustable electrode.

In a further embodiment the power generating assembly comprises a diode device comprising a plurality of electrodes having surfaces substantially facing one another, and a respective spacer or plurality of spacers disposed between said electrodes to allow gaps between said electrodes, and where the surface area of the spacer or plurality of spacers in contact with said surface is less than the surface are of said surfaces.

In a further embodiment the power generating assembly comprises a diode device having one or more electrodes comprising a substantially plane slab of a metal having on one surface one of more indents of a depth approximately 5-20 times a roughness of said surface and a width approximately 5-15 times said depth. In a further embodiment, the one or more electrodes have a periodically repeating structure comprised of said indents such that the work function of said diode device is substantially lower than a diode device that does not comprise said periodically repeating surface structure.

The present invention further contemplates a method for generating electricity comprising the steps of: disposing a diode device at a location within a living organism, wherein said location comprises a temperature differential; generating an electrical current from the temperature differential; charging the electrical circuit with the electrical current.

A technical advantage of the present invention is its ability to provide continuous power.

Another advantage of the present invention is its compatibility with the use of magnetic resonance imaging.

A further advantage of the present invention is to provide possible automatic recharging of medical implants, thereby providing continuous treatment of chronic disease.

Another advantage of the present invention is that the generator does not require surgical removal in order to be recharged. This results in improved quality of life for a patient by minimizing the time spent in the hospital and the risks involved in surgery.

A further technical advantage of the present invention is its efficiency. Such a device has been projected to achieve 70-80% of Carnot efficiency, meaning that with a temperature differential of only 2 degrees Celsius across the device, it could produce a power output of at least 0.005 watts per watt of heat. As the temperature difference between a hot and cold side grows larger, more power can be extracted, and thus with a differential of 5 degrees Celsius, an electrical output of 0.011 watts per watt of heat could be achieved.

Further objects and advantages will become apparent from a consideration of the ensuing description and drawings.

BRIEF DESCRIPTION OF THE SEVERAL VIEWS OF THE DRAWING

For a more complete understanding of the present invention and the technical advantages thereof, reference is made to the following description taken with the accompanying drawings, in which:

FIGS. 1-5 refer to prior art inventions, and:

DETAILED DESCRIPTION OF THE INVENTION

Figure 7:
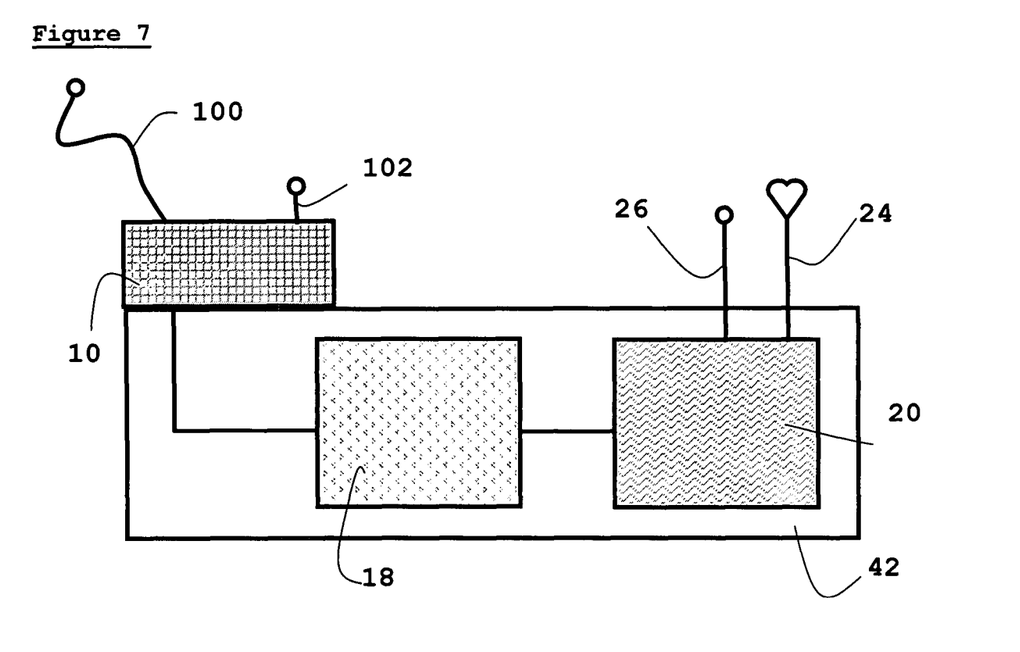
FIG. 7 is a block diagram displaying the basic elements of this invention.

Referring now to FIG. 7, a block diagram is depicted, displaying the basic elements of one preferred embodiment of the present invention. Enclosed within case 42 are implantable device 20, which may further include pacing leads 24 or conduit 26, battery 18, and diode device 10. The depicted assembly is implanted within a patient and utilizes a difference in temperature to generate power that can be harnessed for a wide range of devices and functions. Among its many possible functions, this biothermally powered diode device can power a medical device that responds to various medical needs by providing drug delivery, electrical stimulation, or other forms of assistance. Alternatively, nonmedical devices and other devices, could be provided with electrical energy.

Since the present invention utilizes a temperature differential to generate energy, it must be positioned at a location in the body where such a differential is available. A temperature gradient of up to 5 degrees C. can be found between the skin surface and the body core, and thus, placing the present invention beneath the skin and extending towards the body core is preferred. Another possible configuration would be to have diode device 10 at a distance from case 42 and all it contains, but connected by means of a lead.

As previously discussed, diode device 10 consists of a thermionic or themotunneling converter having two matching electrodes facing one another. Voltage is created when there is a difference in temperature between the two surfaces of the device. It is preferred that diode device 10 be a thermionic or thermotunneling converter consisting of two silicon electrodes maintained at a desired distance from one another by means of spacers, as can be seen in FIGS. 1. Alternatively, a further preferred form of diode device 10 would be the thermionic vacuum diode device with adjustable electrodes in which the separation between the electrodes is set and controlled through the use of piezo-electric positioning elements that is depicted in FIGS. 2 through 4, and as is disclosed in U.S. Pat. No. 6,720,704. An even further preferred form of diode device 10 would be to utilize the method described in U.S. Patent App. No. 2005/0147841 for creating the electrodes in which indents and/or protrusions are etched into the wafer surface by means of laser, chemical, or other etching methods, as seen in FIGS. 5 and 6.

Battery 18 functions as a storage element wherein voltage produced by the diode device can be stored. In times when leads 100 and 102 do not maintain a temperature difference and therefore do not produce any electrical current, the electrical energy stored within battery 18 can supply power to implantable device 20.

Figure 8:
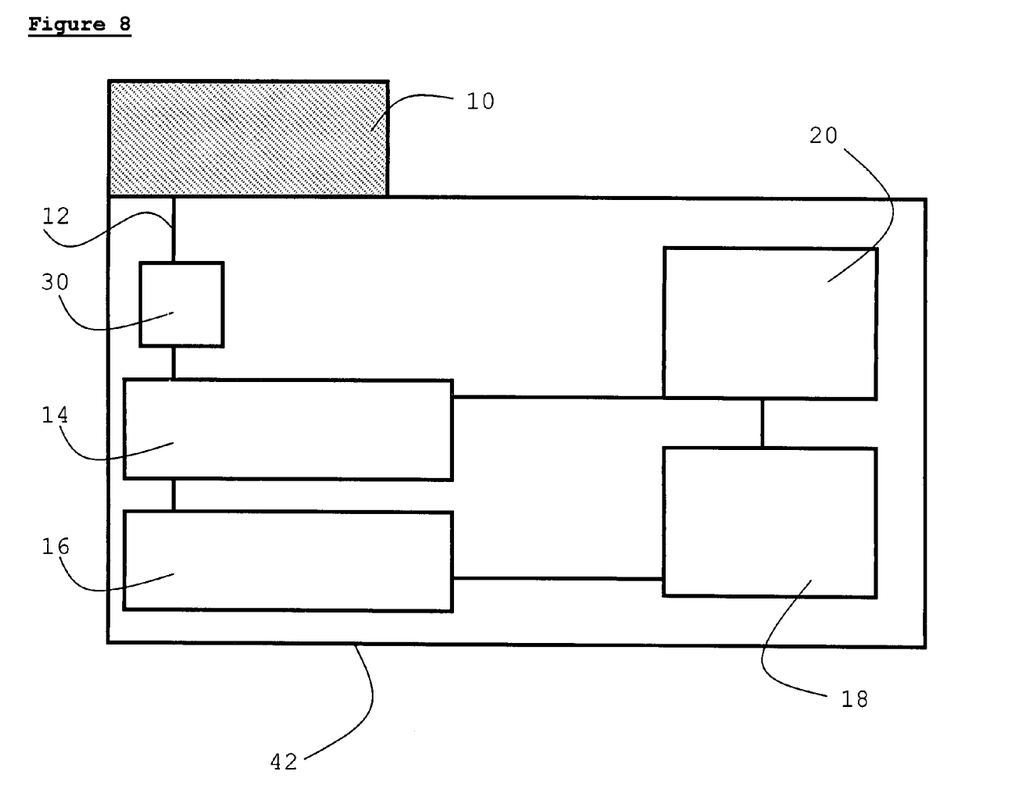
FIG. 8 is a block diagram of a preferred embodiment of this invention.

FIG. 8 is a block diagram displaying the power generator of FIG. 7 with the addition of elements that may be added, either independently or in combination, to enhance the functioning of the biothermal power generator. In the preferred embodiment depicted in FIG. 8, diode device 10 is connected to and provides electrical current to control circuit 14 through lead 12. Control circuit 14, in turn, is operatively connected to voltage regulator 16, which provides direct current to battery 18. Battery 18, in turn, provides power to the implantable device 20. Alternatively, voltage regulator 16 could provide electrical current directly to implantable device 20.

If the temperature on a first surface of diode device 10 is higher than the temperature on the second surface of diode device 10, then the polarity of the produced electric current produced will be the opposite of the situation than when the temperature of the first surface is lower than the temperature of the second surface. Therefore, leads 12 may first communicate with polarity reverser 30 before they are connected with control circuit 14. Through the use of a polarity reversal device 30, electrical current will effectively flow into control circuit 14 under all conditions of temperature.

Figure 9:
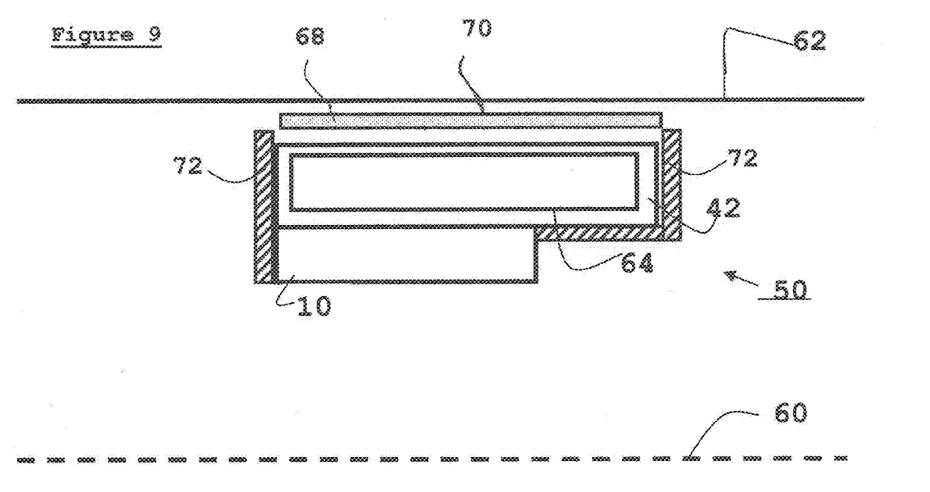
FIG. 9 is a schematic of one preferred device of this invention with its placement near the skin surface.

FIG. 9 is a schematic of one preferred device of this invention in which some unnecessary details have been omitted for simplicity of illustration. In the preferred embodiment depicted in FIG. 9, the assembly 50 utilizes the diode device 10, which may be any of the devices described in FIGS. 1-6, generating electrical current from the temperature gradient between the internal body core 60 and the skin surface 62. Usually the body core temperature is greater than the skin surface temperature, but even in cases where this relationship is reversed, a control circuit 14 (not shown, see FIG. 8) will reverse the polarity of its voltage regulator so the battery can continue to be recharged.

Referring again to FIG. 9, the implant comprises a primary device 64 and a diode device 10. Primary device 64 is comprised of the implantable device 20 and all elements enhancing the implantable device such as those depicted in FIG. 8, with the exception of the diode device 10. Encompassing primary device 64 is a case 42, which provides a hermetic seal around all the entire apparatus while allowing for the passage of wires without breaching the hermetic seal, and has specialized thermal properties that can be achieved by the usage of precise combinations of a variety of materials and fabrication methods. Depending on the desired result, properties such as strength, durability, high thermal conductivity, biocompatibility, magnetic impermeability, and flexibility can be built into the case. Preferably, the diode device 10 is situated immediately against the case 42 and is in thermal contact therewith. The entire assembly is disposed close to the skin surface, and the case 42 may or may not be in direct contact with the skin. In a preferred embodiment, a layer of gel or polymer 68 is planted directly above the device case 42 and is contained within a conductive sealing membrane 70. Both gel 68 and membrane 70 provide a highly thermally conductive path from the device case 42 to the skin surface 62 as well as creating a greater degree of comfort for the patient.

Another feature that may be added to assembly 50 to thermally isolate it from the surrounding environment is an insulating sheath. In FIG. 9, and the preferred embodiment depicted therein, insulating sheath 72 surrounds primary device 64 and is made preferably of a flexible polymeric insulating material.

One benefit of assembly 50 being disposed immediately below the skin surface is the capacity for heat to be added or removed from one side of the diode device through the use of an external hot (or cold) source. By way of example, a patient could apply an ice pack or a warming apparatus to the skin surface directly above the implanted medical device, creating a greater temperature differential between the two surfaces of the diode device, and thus providing increased electrical current to the implantable device. In this way, a patient could ensure a plentiful supply of electrical current to the implanted device regardless of the ambient temperature.

Figure 10:
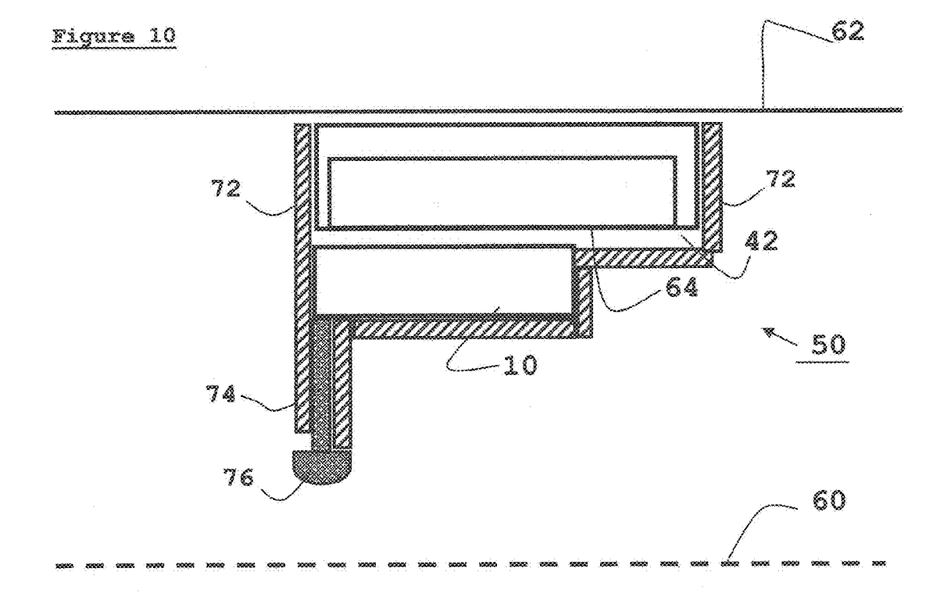
FIG. 10 is a schematic of one preferred device of this invention with a further preferred placement near the skin surface.

FIG. 10 is a schematic of another preferred design of assembly 50. Like FIG. 9, it generates electrical current through the temperature differential between the body core and the skin surface. Many of the components are similar in design and function to the corresponding components described in FIG. 9. However, in this preferred embodiment, gel/polymer 68 and its membrane 70 have been removed, and device case 42 is now in direct contact with the skin. Furthermore, an inward facing portion of the device 50 has been extended towards the body core 60 to enhance current generation by contacting a region with a greater average temperature. A conductive rod 74, which may be a rod or heat pipe, extends from the diode device 10 towards the body's center and ends in a thermal contact 76. The insulating sheath 72 of FIG. 8 has been extended along the length of rod 74, maintaining thermal isolation from the surrounding body tissue. The design depicted in FIG. 9 is meant to provide for a greater temperature differential, and thus a greater current generation.

There exist a multiplicity of variations for the positioning, size, and comfort of the implant that may or may not make use of design features such as a conformable gel or polymer between the device and the skin, insulating sheath, conductive plates and other electrical features that will be obvious to those skilled in the art.

Figure 11:
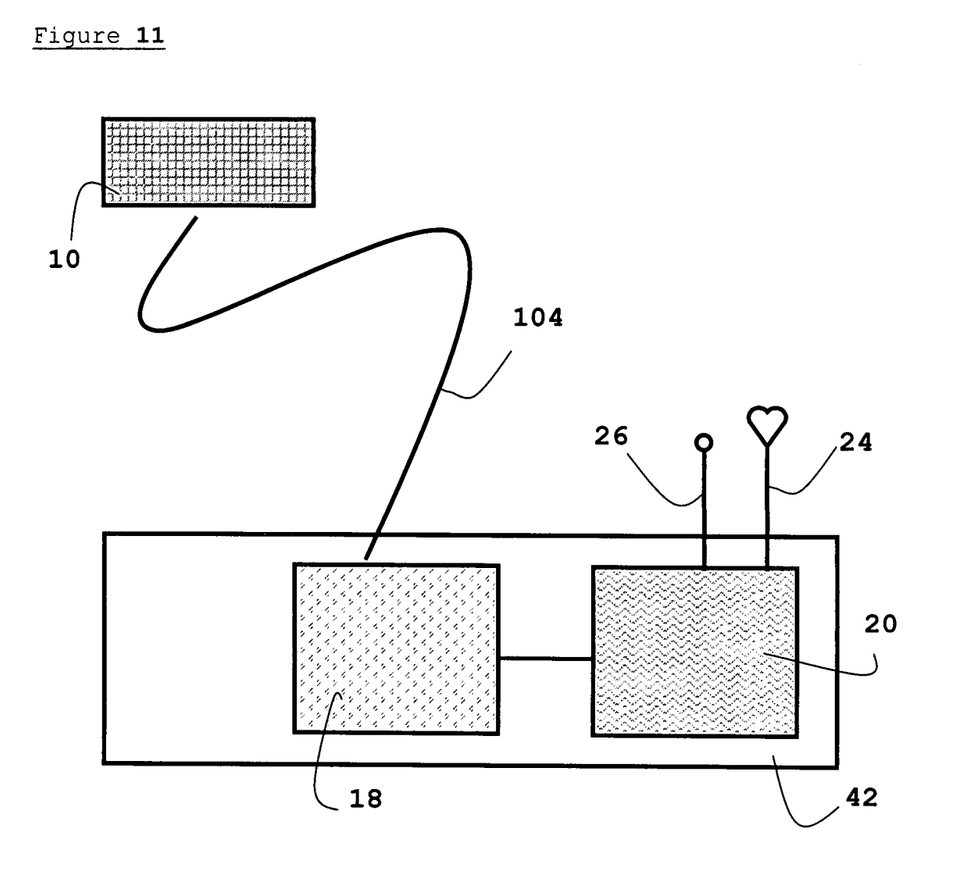
FIG. 11 is a schematic of a further preferred embodiment of this invention in which the diode device is at a distance from the implantable device.

FIG. 11 is a further preferred embodiment of the present invention in which the diode device is placed at a distance from the implantable circuitry to which it provides power. An advantage of such a configuration is that the diode device could be positioned at a location that provides the greatest possible temperature gradient while the circuitry it powers could be positioned at a second location that provides for greater comfort, ease of installation, repair, and monitoring, or other advantages. In FIG. 11, diode device 10 is connected to primary device 64 via electrically conducting lead 104.

While this invention has been described with reference to numerous embodiments, it is to be understood that this description is not intended to be construed in a limiting sense. It will be obvious to persons skilled in the art that the biothermal power generation process described herein encompasses numerous embodiments in which there are changes in the details of the present invention and additional embodiments of the present invention will be apparent to, and may be made by, persons of ordinary skill in the art having reference to this description. It is to be understood that all the embodiments described above can be utilized in any possible combination. It is contemplated that all such changes and additional embodiments are within the spirit and true scope of the invention as claimed below.

The invention claimed is:

1. An improved biothermal power generating assembly adapted for implantation in a living organism comprising:
   a. a thermionic or thermotunneling vacuum diode device designed to generate with improved efficiency from a temperature gradient within a living organism a substantially continuous supply of electric energy from said temperature gradient, wherein said thermionic or thermotunneling vacuum diode device comprises two spaced silicon electrodes with matching facing surfaces facing one another and maintained at a desired spaced distance from one another by spacer elements comprising a respective spacer or plurality of spacers disposed between said electrode facing surfaces to maintain the desired spaced distance between said electrode facing surfaces and positioned to maintain said desired spaced distance, and wherein each of said electrodes is adapted to be in direct thermal contact with a part of said organism having a different temperature to produce a temperature differential between said electrodes and efficiently generate said substantially continuous supply of electric energy;
   b. an implantable device in direct electric communication with said thermionic or thermotunneling vacuum diode device and adapted to be operated efficiently by said substantially continuous supply of electric energy;
   c. electric power storage means in electric communication with said vacuum diode device and said implantable device for storing electric energy generated by said vacuum diode device and providing electric energy to said implantable device means when said vacuum diode device electrodes do not maintain a temperature differential capable of generating sufficient electric energy to operate said implantable device; and
   d. an implantable assembly housing designed adapted to be implanted in a living organism so that said electrodes are in direct thermal contact with parts of said organism having different temperatures.

2. The biothermal power generating assembly of claim 1, wherein said vacuum diode device is a thermionic diode device, said spacer elements are piezo-electric positioning elements, and the desired distance between said electrodes is adjustable with said piezo-electric positioning elements.

3. The biothermal power generating assembly of claim 1, wherein said electric power storage means is a battery.

4. The biothermal power generating assembly of claim 1, further comprising sensor means in communication with said vacuum diode device for sensing temperatures of said living organism, both at an external surface and internally and communicating each sensed temperature to a one of said spaced electrodes.

5. The biothermal power generating assembly of claim 1, wherein said implantable device comprises a cardiac assist device.

6. The biothermal power generating assembly of claim 1, wherein said assembly is configured to be implantable beneath an external surface of the organism's external body surface or skin so that one of said electrodes is in direct thermal contact with said external body surface and the other of said electrodes is in direct thermal contact with a part of the organism's body core having a different temperature from the external surface.

7. The biothermal power generating assembly of claim 6, wherein said assembly housing further comprises flexible insulating means for thermally isolating said assembly from a living organism environment in which it is implanted.

8. The biothermal power generating assembly of claim 1, wherein said biothermal power generating assembly is configured adapted to be implantable within a human body.

9. The biothermal power generating assembly of claim 1, wherein said vacuum diode device is located outside said assembly housing and at a distance from said implantable device and said electric power storage means, wherein said distance is selected to maximize the temperature differential between said electrodes.

10. The biothermal power generating assembly of claim 1, wherein said assembly further comprises control circuit means in electric communication with said vacuum diode device; voltage regulator means operatively connected to said control circuit means to provide electric current to said electric power storage means or to said implantable device means; and polarity reverser means in electric communication with said vacuum diode device and said control circuit means for maintaining a flow of electric current into said control circuit means under all temperature differential conditions.

11. The biothermal power generating assembly of claim 10, wherein said polarity reverser means maintains said flow of electric current by selectively reversing the polarity of said electrical current when a temperature differential exists between said electrodes.

12. The biothermal power generating assembly of claim 1, wherein said vacuum diode device is positioned to be located internally of said implantable assembly housing in a subcutaneous location in said organism, and said biothermal power generating assembly further comprises a conductive rod with a thermal tip in thermal contact with one of said electrodes and positioned to extend toward an internal location within said organism's body with a higher temperature than a temperature of said subcutaneous location, thereby maximizing and enhancing efficient electric current generation from the temperature differential between said subcutaneous and said internal locations.

13. The biothermal power generating assembly of claim 1, wherein said electrode matching facing surfaces comprise a series of a regularly repeating pattern of indents that maintain said desired spaced distance, and said indents have a depth approximately 5-20 times a roughness of said surfaces and a width approximately 5-15 times said depth.

14. The biothermal power generating assembly of claim 13, wherein the series of indents has a width on the order of 2 µm or less and a depth on the order of 20 nm or less, wherein the work function of said vacuum diode device is substantially lower than a vacuum diode device with electrodes with surfaces without said periodically repeating structure of indents.

15. The biothermal power generating assembly of claim 1, wherein said spacer elements comprise dots of silicon oxide.

16. A method comprising generating with improved efficiency a substantially continuous supply of electric energy from a temperature differential existing at different locations within a living organism, further comprising:
  a. providing, in a biothermal power generating assembly adapted to be implanted within a living organism, a thermionic or thermotunneling converter vacuum diode device designed to use a temperature differential in a living organism to generate with improved high efficiency a substantially continuous supply of electric energy from said temperature differential, said vacuum diode device comprising matching silicon electrodes with matching surfaces facing one another and maintained spaced apart from one another a desired distance by spacer elements;
  b. producing a temperature differential between said electrodes by adapting said electrodes so that each electrode is in direct thermal contact with a part of a living organism having a different temperature;
  c. generating through the matching spaced electrodes, wherein each said electrode has a different temperature corresponding to a temperature of a different part of the living organism, a substantially continuous supply of electric energy from said temperature differential at an improved efficiency in the range of 70-80% of Carnot; and
  d. directing said substantially continuous supply of electric energy to a device implantable in a living organism requiring a supply of electric energy to substantially continuously operate said implantable device within said living organism.

17. The method of claim 16, wherein said implantable device is a medical device and is operated by said substantially continuous supply of electric energy to provide drug delivery, cardiac assistance, or electrical stimulation.

18. The method of claim 16, wherein said implantable device is a medical device useful in humans, and said biothermal power generating assembly is implanted so that one electrode is adapted to be in direct thermal contact with a human's skin and one electrode is adapted to be in direct thermal contact with a human's body core, thereby maximizing the temperature difference between said electrodes and the supply of electric energy efficiently produced by said diode device.

19. The method of claim 16, wherein when said temperature differential between said electrodes is 2° Celsius, at least 0.005 Watts of electric energy per Watt of heat is generated.

20. The method of claim 16, wherein when said temperature differential between said electrodes is 5° Celsius, at least 0.011 Watts of electric energy per Watt of heat is generated.

* * * * *